(12) United States Patent
DeVore et al.

(10) Patent No.: US 6,217,575 B1
(45) Date of Patent: Apr. 17, 2001

(54) PMR CATHETER

(75) Inventors: Lauri DeVore, Seattle; Bryan Kinsella, Mukilteo, both of WA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/256,831

(22) Filed: Feb. 24, 1999

(51) Int. Cl.$^7$ .................................................. A61B 18/14
(52) U.S. Cl. .............................. 606/41; 606/49; 606/50; 607/99; 607/105; 607/113; 604/22
(58) Field of Search ................... 606/41, 45–50; 607/99, 105, 113, 122; 604/22

(56) References Cited

U.S. PATENT DOCUMENTS

| | | | |
|---|---|---|---|
| 5,451,224 | * 9/1995 | Goble et al. | 606/48 |
| 5,593,406 | * 1/1997 | Eggers et al. | 606/46 |
| 5,766,164 | 6/1998 | Mueller et al. | 606/15 |
| 5,769,843 | 6/1998 | Abela et al. | 606/10 |
| 5,782,823 | 7/1998 | Mueller | 606/7 |
| 5,785,702 | 7/1998 | Murphy-Chutorian et al. | 606/7 |
| 5,800,450 | 9/1998 | Lary et al. | 606/180 |
| 5,807,384 | 9/1998 | Mueller | 606/7 |
| 5,807,388 | 9/1998 | Jeevanandam et al. | 606/15 |
| 5,810,836 | 9/1998 | Hussein et al. | 606/108 |
| 5,827,203 | 10/1998 | Nita | 601/2 |
| 5,832,929 | 11/1998 | Rudko et al. | 128/898 |
| 5,840,059 | 11/1998 | March et al. | 604/53 |
| 5,840,075 | 11/1998 | Mueller et al. | 606/7 |
| 5,855,577 | 1/1999 | Murphy-Chutorian et al. | 606/7 |
| 5,860,951 | 1/1999 | Eggers et al. | 604/49 |
| 5,871,469 | 2/1999 | Eggers et al. | 604/114 |
| 5,871,495 | 2/1999 | Mueller | 606/185 |
| 5,873,366 | 2/1999 | Chim et al. | 128/898 |
| 5,873,855 | 2/1999 | Eggers et al. | 604/114 |
| 5,878,751 | 3/1999 | Hussein et al. | 128/898 |
| 5,885,272 | 3/1999 | Aita et al. | 606/7 |
| 5,885,276 | 3/1999 | Ammar et al. | 606/21 |
| 5,891,133 | 4/1999 | Murphy-Chutorian | 606/7 |
| 5,893,848 | 4/1999 | Negus et al. | 606/41 |
| 5,906,615 | * 5/1999 | Thompson | 606/45 |
| 6,093,185 | * 7/2000 | Ellis et al. | 607/122 |

FOREIGN PATENT DOCUMENTS

| | | |
|---|---|---|
| 0 868 923 A2 | 10/1998 | (EP) . |
| WO 98/19614 | 5/1998 | (WO) . |
| WO 98/25533 | 6/1998 | (WO) . |
| WO 98/27877 | 7/1998 | (WO) . |
| WO 98/30144 | 7/1998 | (WO) . |
| WO 98/31281 | 7/1998 | (WO) . |
| WO 98/33557 | 8/1998 | (WO) . |
| WO 98/38916 | 9/1998 | (WO) . |
| WO 98/38925 | 9/1998 | (WO) . |
| WO 98/39038 | 9/1998 | (WO) . |
| WO 98/49963 | 11/1998 | (WO) . |
| WO 98/49964 | 11/1998 | (WO) . |
| WO 99/04708 | 2/1999 | (WO) . |
| WO 99/04709 | 2/1999 | (WO) . |
| WO 99/07296 | 2/1999 | (WO) . |
| WO 99/08612 | 2/1999 | (WO) . |

* cited by examiner

*Primary Examiner*—Lee Cohen
(74) *Attorney, Agent, or Firm*—Crompton, Seager & Tufte, LLC

(57) ABSTRACT

Devices and methods for performing percutaneous myocardial revascularization (PMR). A catheter in accordance with the invention includes an elongate shaft having a proximal end and a distal end. The elongate shaft defines a lumen, and a conductor is disposed inside the lumen. An electrode portion is formed by the bent portion of the conductor which extends from the distal end of the elongate shaft. A method in accordance with the present invention may be used to form a wound through the endocardium and into the myocardium of a patient's heart. Collateral damage to the myocardium may be created by infusing pressurized fluid into the wound. A number of fluids may be delivered to a location proximate the wound via the catheter.

33 Claims, 8 Drawing Sheets

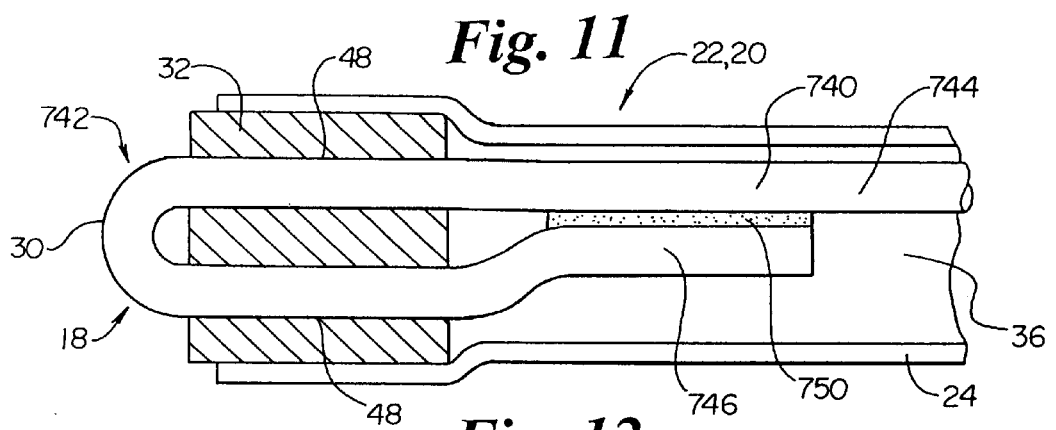
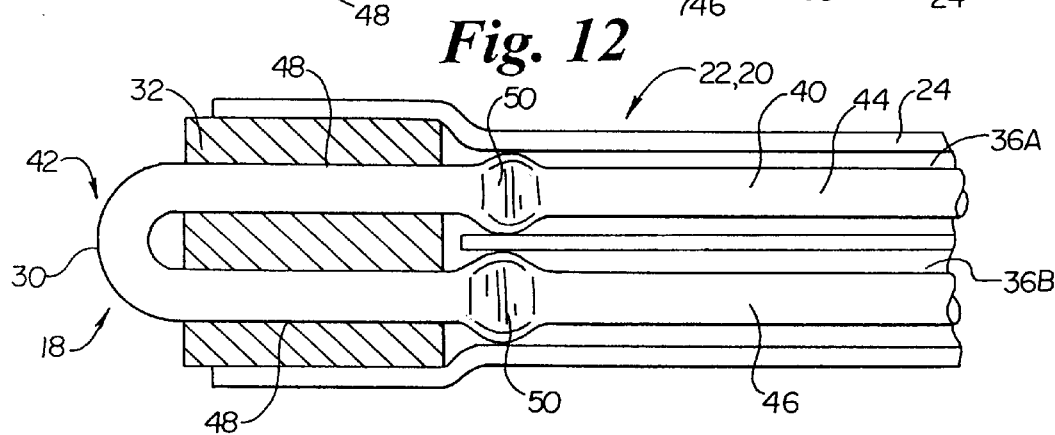
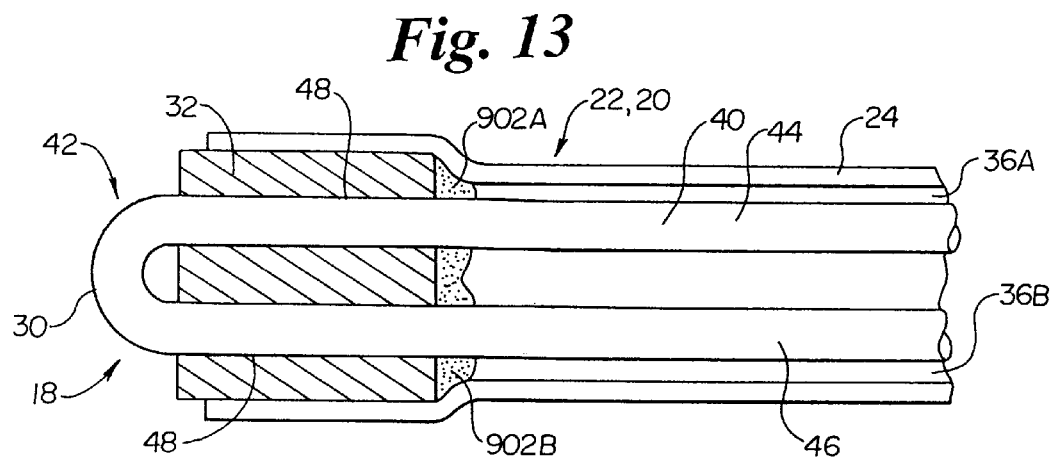

PMR CATHETER

RELATED APPLICATION

The present application is related to U.S. patent application Ser. No. 09/256,958, filed by the same assignee on even date herewith and entitled "Device and Method for Percutaneous Myocardial Revascularization."

FIELD OF THE INVENTION

The present invention relates generally to devices and methods for promoting blood circulation to the heart muscle. More particularly, the present invention relates to devices and methods for forming holes or channels in the walls of a heart chamber such as those created during a percutaneous myocardial revascularization (PMR) procedure.

BACKGROUND OF THE INVENTION

Assuring that the heart muscle is adequately supplied with oxygen is critical to sustaining the life of a patient. To receive an adequate supply of oxygen, the heart muscle must be well perfused with blood. In a healthy heart, blood perfusion is accomplished with a system of blood vessels and capillaries. However, it is common for the blood vessels to become occluded (blocked) or stenotic (narrowed). A stenosis may be formed by an atheroma which is typically a harder, calcified substance which forms on the walls of a blood vessel.

Historically, individual stenotic lesions have been treated with a number of medical procedures including coronary bypass surgery, angioplasty, and atherectomy. Coronary bypass surgery typically involves utilizing vascular tissue from another part of the patient's body to construct a shunt around the obstructed vessel. Angioplasty techniques such as percutaneous transluminal angioplasty (PTA) and percutaneous transluminal coronary angioplasty (PTCA) are relatively non-invasive methods of treating a stenotic lesion. These angioplasty techniques typically involve the use of a guidewire and a balloon catheter. In these procedures, a balloon catheter is advanced over a guidewire such that the balloon is positioned proximate a restriction in a diseased vessel. The balloon is then inflated and the restriction in the vessel is opened. A third technique which may be used to treat a stenotic lesion is atherectomy. During an atherectomy procedure, the stenotic lesion is mechanically cut or abraded away from the blood vessel wall.

Coronary bypass, angioplasty, and atherectomy procedures have all been found effective in treating individual stenotic lesions in relatively large blood vessels. However, the heart muscle is perfused with blood through a network of small vessels and capillaries. In some cases, a large number of stenotic lesions may occur in a large number of locations throughout this network of small blood vessels and capillaries. The torturous path and small diameter of these blood vessels limit access to the stenotic lesions. The sheer number and small size of these stenotic lesions make techniques such as cardiovascular bypass surgery, angioplasty, and atherectomy impractical When techniques which treat individual lesions are not practical a technique know as percutaneous myocardial revascularization (PMR) may be used to improve the oxygenation of the myocardial tissue. A PMR procedure generally involves the creation of holes, craters or channels directly into the myocardium of the heart. PMR was inspired in part by observations that reptilian heart muscles are supplied with oxygen primarily by blood perfusing directly from within heart chambers to the heart muscle. This contrasts with the human heart, which is supplied by coronary vessels receiving blood from the aorta. Positive clinical results have been demonstrated in human patients receiving PMR treatments. These results are believed to be caused in part by blood flowing within a heart chamber through channels in myocardial tissue formed by PMR. Increased blood flow to the myocardium is also believed to be caused in part by the healing response to wound formation. Specifically, the formation of new blood vessels is believed to occur in response to the newly created wound. This response is sometimes referred to as angiogenisis. In addition to promoting increased blood flow, it is also believed that PMR improves a patient's condition through denervation. Denervation is the elimination of nerves endings. Specifically, the creation of wounds during a PMR procedure results in the elimination of nerve endings which were previously sending pain signals to the brain as a result of hibernating tissue.

SUMMARY OF THE INVENTION

The present invention pertains to devices and methods for performing percutaneous myocardial revascularization (PMR). A device in accordance with the present invention may be used to form wounds in the myocardium of a patient's heart. Several general types of wounds may be created with this device. For example, this device may be used to form a channel wound (e.g., a wound with a depth greater than its width). By way of a second example, this device may be used to form a crater wound (e.g., a wound with a width greater than its depth).

In a preferred embodiment, a catheter in accordance with the present invention includes an elongate shaft having a proximal end and a distal end. The elongate shaft defines a lumen which extends substantially through the elongate shaft. An insulator is fixably attached to the elongate shaft at its distal end. The insulator includes at least two holes. The catheter also includes a conductor having a bent portion, a first leg portion and a second leg portion. The first and second leg portions of the conductor pass through the holes of the insulator and are disposed in the lumen of the catheter. The bent portion of the conductor substantially forms an electrode protruding from the distal end of the catheter.

The distance which the electrode protrudes from the insulator is carefully controlled during the manufacture of the catheter. This helps to control the depth of the wounds which will be created with the catheter during a PMR procedure. In a presently preferred embodiment of the present invention, the electrode proceeds to penetrate the heart until the insulator contacts the heart tissue.

The insulator includes two landing zones which extend away from the electrode. The width of the landing zones is generally larger than the width of the electrode. The relatively large area of the landing zones assures that the travel of the electrode into the heart will stop when the landing zones contact the heart tissue.

It is a desirable feature of this invention that the landing zones extend beyond the wound created in the heart tissue during a PMR procedure. This is because the wounded tissue is substantially softened, and it is possible for a PMR catheter to be pushed through soft, injured tissue.

The distance which the electrode protrudes from the landing zone and the relative surface areas of these elements are carefully selected to create a therapeutically effective wound while reducing the likelihood of unintentionally perforating the myocardium. Preferably, a therapeutically effective wound will, at a minimum, perforate through the endocardium and damage blood vessels and capillaries in the myocardium. The likelihood of unintentionally perforating through the myocardium to the epicardium is reduced when the depth of the wound created is only enough to penetrate the endocardium adjacent the myocardium.

In one embodiment of a device in accordance with the present invention, the conductor defines a conductor lumen and at least one hole in fluid communication with the conductor lumen. The conductor lumen may be used during a PMR procedure to deliver fluid to the distal end of the catheter. The fluid delivered during the PMR procedure may include contrast, saline, therapeutic agents, etc. The fluid may be used for a number of tasks, including mapping a heart, marking an injury site or promoting angiogenic effects.

In a presently preferred method in accordance with the present invention, pressurized fluid may be delivered to the wound site during or after wound formation. The formation of the wound may be enhanced by collateral damage to the myocardium induced by directing this pressurized fluid into the wound site. The impact of pressurized fluid causes vessels, capillaries and sinuses to rupture. By creating this collateral damage, the number of wounds which need be made during a PMR procedure may be substantially reduced. A second benefit of this collateral damage is that the depth of the wounds required to achieve a therapeutic effect may be reduced. In addition, the injection of contrast creates a fluoroscopic marker of the treatment location.

BRIEF DESCRIPTION OF THE DRAWINGS

FIG. 11 is a plan view of the distal end of a catheter in accordance with the present invention with the catheter being shown in partial cross section;

FIG. 12 is a plan view of the distal portion of a catheter in accordance with the present invention with the catheter being shown in partial cross section;

FIG. 13 is a plan view of the distal portion of a catheter in accordance with the present invention with the catheter being shown in partial cross section;

DETAILED DESCRIPTION OF THE INVENTION

The following detailed description should be read with reference to the drawings, in which like elements in different drawings are numbered identically. The drawings which are not necessarily to scale, depict selected embodiments and are not intended to limit the scope of the invention.

Examples of constructions, materials, dimensions, and manufacturing processes are provided for selected elements. All other elements employ that which is known to those of skill in the field of the invention. Those skilled in the art will recognize that many of the examples provided have suitable alternatives which may be utilized.

Figure 1:
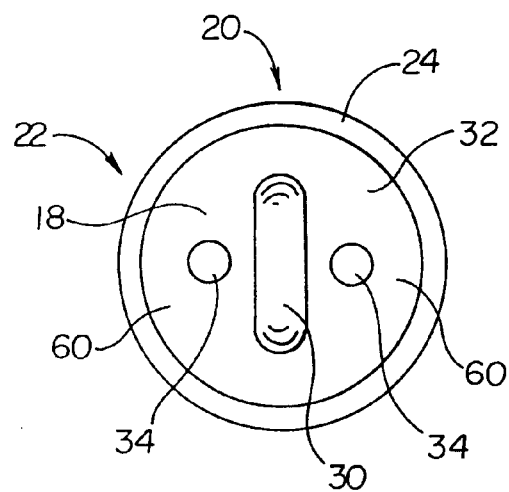
FIG. 1 is a plan view of the distal end of a catheter in accordance with the present invention.
Figure 2:
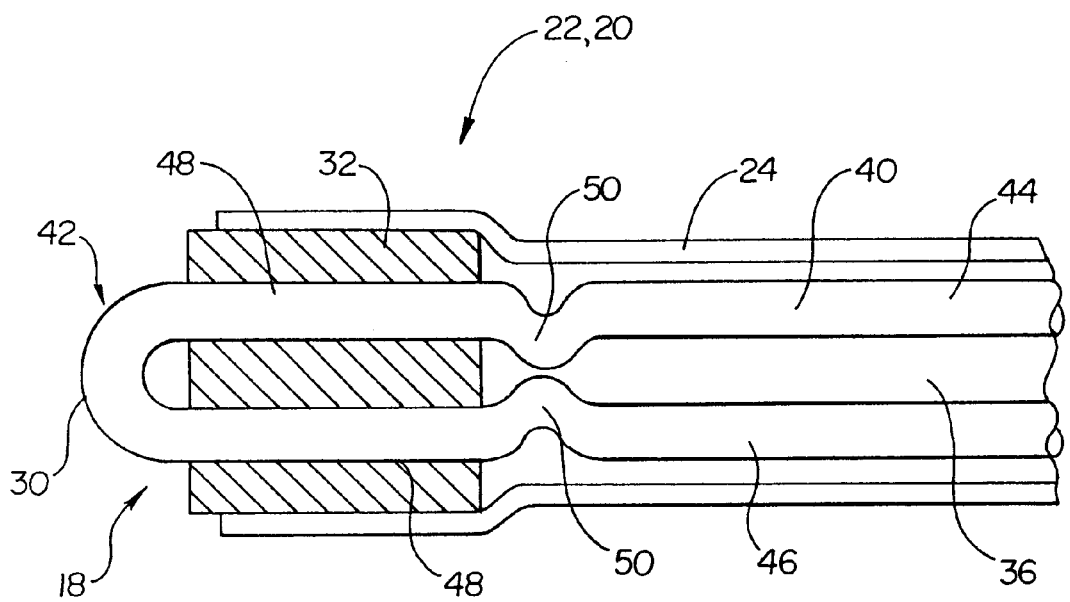
FIG. 2 is a plan view of the distal portion of a catheter in accordance with the present invention with the catheter shown in partial cross section.

FIGS. 1 and 2 are plan views of a catheter 20 in accordance with the present invention. FIG. 1 is a plan view of a distal end 18 of catheter 20. Catheter 20 includes an elongate shaft 24, a proximal end 26 (not shown) and a distal portion 22. An electrode portion 30 and an insulator 32 are disposed proximate distal end 18 of catheter 20. Insulator 32 includes a plurality of insulator lumens 34.

In FIG. 2 a distal portion of catheter 20 is shown in partial cross-section. In FIG. 2, it can be appreciated that elongate shaft 24 includes a shaft lumen 36. Catheter 20 includes a conductor 40 having a bent portion 42, a first leg 44, and a second leg 46. First leg 44 and second leg 46 are disposed in lumen 36 of elongate shaft 24. As is best shown in FIG. 2, electrode 30 of catheter 20 is generally formed from bent portion 42 of conductor 40. As also shown in FIG. 2, insulator 32 defines two holes 48 which are adapted to allow legs 44, 46 of conductor 40 to pass through insulator 32. In a presently preferred embodiment, conductor 40 is adapted to be connected to a radio frequency generator.

One or more retaining elements 50 are formed on conductor 40 proximate insulator 32. In the embodiment of FIG. 2, retaining elements 50 have been created by forming two kinks in conductor 40. It will be understood that other embodiments of retaining elements 50 are possible without deviating from the spirit or scope of the present invention. It will also be understood that although two retaining elements are shown in FIG. 2, additional embodiments have been envisioned which utilize a single retaining element 50.

As best seen in FIG. 2, electrode 30 protrudes beyond insulator 32 of catheter 20. The distance which electrode 30 protrudes is determined in part by the shape of bent region 42 of conductor 40. The distance which electrode 30 protrudes is carefully controlled during the manufacture of catheter 20. This helps to control the depth of the wounds which are created by catheter 20 during a PMR procedure. During such a procedure electrode 30 will proceed to penetrate the heart until insulator 32 contacts the heart tissue. As best seen in FIG. 1, insulator 32 includes two landing zones 60 which extend away from electrode 30. In the embodiment of FIG. 1, the width of landing zones 60 is substantially greater than the width of electrode 30. The relatively large area of landing zones 60 assures that the travel of electrode 30 into the heart will stop when landing zones 60 contact the heart tissue. It is a desirable feature of this invention that landing zones 60 extend beyond the wound created in the heart tissue during a PMR procedure. This is because the wounded tissue is substantially softened, and it is possible for a PMR catheter to be pushed through soft, injured tissue.

The distance which electrode 30 protrudes from landing zones 60 and the relative surface areas of these elements are carefully selected to create a therapeutically effective wound while reducing the likelihood of unintentionally perforating the myocardium. A therapeutically effective wound generally must perforate the endocardium and damage blood vessels and capillaries in the myocardium. The likelihood of unintentionally perforating the myocardium is reduced when the depth of wound created is only enough to penetrate the endocardium.

By way of example, the dimensions below have been found effective in creating therapeutically effective wounds while reducing the likelihood that the myocardium will be punctured through to the epicardium.

In a presently preferred embodiment the distance electrode 30 protrudes from landing zones 60 is between about 0.005 and about 0.4 inches. In a presently most preferred embodiment the distance electrode 30 protrudes from landing zones 60 is between about 0.010 and about 0.035 inches.

In a presently preferred embodiment, in accordance with FIG. 2, the diameter of conductor 40 in bent portion 42 is between 0.003 and about 0.030 inches. In a presently most preferred embodiment, in accordance with FIG. 2, the diameter of conductor 40 in bent portion 42 is between about 0.008 and about 0.012 inches. It should be understood that the diameter of conductor 40 may vary along its length, and conductor 40 may include one or more tapered sections to optimize shaft support and flexibility. In a presently preferred embodiment, conductor 40 is about 70 inches long having a distal portion with a diameter of about 0.010 inches and a proximal portion with a diameter of about 0.022 inches. In this presently preferred embodiment, conductor 40 includes a transition portion which is about 8 inches long and which tapers from the diameter of the proximal portion to the diameter of the distal portion.

In a presently preferred embodiment in accordance with FIG. 2, the bend radius of electrode 30 is between about 0.004 and about 0.1 inches. In the presently most preferred embodiment in accordance with FIG. 2, the bend radius of electrode 30 is between about 0.012 and about 0.023 inches.

In a presently preferred embodiment the width of landing zones 60 extending from two sides of electrode 30 is between about 0.007 and about 0.050 inches. In a presently most preferred embodiment the width of landing zones 60 extending from two sides of electrode 30 is between about 0.015 and about 0.030 inches. As described above, and shown in FIG. 1, there are two landing zones 60 extending away from electrode 30 in the embodiment of FIGS. 1 and 2.

Although breaking through the endocardium may be sufficient treatment for many patients, for some patients the physician may prefer to penetrate the myocardium with electrode 30 a certain distance. As described previously, the depth which electrode 30 penetrates heart tissue may be controlled by the geometry of electrode 30 and landing zones 60. The distance which electrode 30 protrudes from landing zones 60 is carefully controlled during the manufacture of catheter 20. A number of models of catheter 20 may be supplied to a physician, each model being adapted to produce wounds of a specific depth. The depth of the wound created is influenced by the depth which the electrode penetrates the heart tissue. Other factors may influence the depth of wound created without deviating from the spirit or scope of the present invention. For example, the depth of wound created may be effected by the magnitude and frequency of the radiofrequency energy applied to electrode 30. By way of a second example, the depth of wound produced may be effected by the length of time the electrode is energized.

Conductor 40 and electrode portion 30 may be comprised of stainless steel, Nitinol, or a number of other materials which are conductive and biocompatable. In a presently preferred embodiment, conductor 40 and electrode portion 30 are comprised of Nitinol. Embodiments of electrode 30 have also been envisioned wherein electrode 30 includes a radiopaque material. Examples of radiopaque material which may be included in electrode 30 include: gold, platinum, silver, and tungsten.

Insulator 32 may be formed from ceramic, glass, glass-ceramic, polytetrafluoroethylene (PTFE), polyimide, or a number of other materials which are non-conductive and biocompatible and/or thermally insulated and biocompatible. In a presently preferred embodiment, insulator 32 is formed from ceramic. Further embodiments of insulator 32 have been envisioned which include a radiopaque material. The radiopaque materials which may be suitable for inclusion in an insulator 32 in some embodiments, include: gold, platinum, silver, tungsten, barium sulfide and bismuth oxide. In a presently preferred radiopaque embodiment of insulator 32, a radiopaque material is selectively applied to the outer diameter of insulator 32. A presently preferred radiopaque material is a platinum/iridium blend.

Although conductor 40 in the embodiment of FIGS. 1 and 2 is circular in cross section, it should be understood that other cross-sectional shapes are possible without deviating from the spirit or scope of the invention. For example, the cross-sectional shape of conductor 40 could be rectangular, square, triangular, oval, etc.

In a presently preferred embodiment, elongate shaft 24 is comprised of polyether block amide (PEBA). Polyether block amide is commercially available from Atomchel Polymers of Birsdsboro Pennsylvania under the trade name PEBAX. Elongate shaft 24 may be comprised of other materials without departing from the spirit of scope of this invention. Examples of materials which may be suitable in some applications include: polyethylene (PE), polypropylene (PP), polyvinylchloride (PVC), polyurethane, polyimide, and polytetrafluoroethylene (PTFE).

As described above, in a presently preferred embodiment, insulator 32 and elongate shaft 24 are separate elements comprised of ceramic and PEBA respectively. However, it should be understood that these two elements could be combined into one element formed of one material without deviating from the spirit or scope of the present invention. In the embodiment of FIGS. 1 and 2, elongate shaft 24 has a single lumen 36. It will be understood that embodiments of the present invention have been envisioned in which shaft 26 has multiple lumens 36.

During a PMR procedure, catheter 20 is preferably advanced through the vasculature of a patient until distal end 18 is proximate the endocardium of a patient's heart. The route taken by catheter 20 will normally be by way of the femoral artery and the aorta to the left ventricle.

Those of skill in the art will appreciate that other routes may be taken without deviating from the spirit or scope of the present invention. For example, catheter 20 may enter the right ventricle by way of the pulmonary vein or femoral vein. As a second example of an alternate route which may be taken by catheter 20, catheter 20 may enter the right ventricle from the left ventricle by passing through the septal wall. As a third example of an alternate route which may be taken by catheter 20, catheter 20 may enter the body at the carotid artery and reach the heart therethrough.

To facilitate the advancement of catheter 20 through the vasculature of the patient, catheter 20 may include a slippery material disposed on the outer surfaces of elongate shaft 24. Once inside the heart, distal end 18 of catheter 20 is positioned proximate the endocardium, preferably, such that electrode portion 30 is in contact with the endocardium. Electrode portion 30 may then be energized to form a wound.

Typically, an additional step in a method in accordance with the present invention is to identify areas of tissue within the patient's heart which are candidates for PMR. To facilitate ease of discussion, areas of tissue in the heart muscle may be generally classified healthy or hibernating. Healthy tissue is tissue which is well perfused with blood, and subsequently well supplied with oxygen. Hibernating tissue is tissue which is not currently contracting to assist in the pumping of blood. However, if hibernating tissue is adequately supplied with blood, it will once again begin contracting and contribute to the pumping of blood.

A number of methods may be used to identify hibernating tissue. For example, contrast media may be injected into the coronary vessels to identify regions of the heart into which the contrast medium does not flow due to obstruction of the vessels into which the media was injected. In this case, the hibernating region will be identified by the lack of flow or abnormally low flow distally of the obstruction in the coronary vessel or vessels.

A second method which may be used to identify hibernating regions of the heart involves injecting contrast media directly into the heart chambers. Hibernating tissue may then be identified by locating areas of generally poor wall motion of the heart chambers. When this method is selected, the contrast media may be delivered to the heart chambers via catheter 20. Shaft lumen 36 and insulator lumens 34 of catheter 20 provide a suitable channel for delivering contrast media from a location outside the patient's body to distal end 18 of catheter 20.

Once hibernating regions within the heart are identified, these regions may be targeted for PMR. Electrode 30 will be positioned proximate the targeted heart tissue. In a presently preferred method, a contact detecting means in conjunction with electrode 30 will be used to sense contact between electrode 30 and heart tissue. This method is further detailed in a co-pending U.S. patent application Ser. No. 09/256,958, filed by the same assignee on even date herewith and entitled "Device and Method for Percutaneous Myocardial Revascularization."

During a PMR procedure, electrode 30 will proceed to penetrate the heart until landing zones 60 of insulator 32 contact the heart tissue. As described above, landing zones 60 have a relatively large surface area to assure that the depth of electrode penetration will be controlled. The depth of the wound is also influenced by the distance which electrode 30 protrudes from landing zones 60. As described above, this distance is carefully controlled during the manufacture of catheter 20.

As described above, the distance which electrode 30 protrudes from landing zones 60 and the relative surface areas of these elements are carefully selected to create a therapeutically effective wound while reducing the likelihood of unintentionally perforating the myocardium. Preferably, a therapeutically effective wound will perforate through the endocardium and damage blood vessels and capillaries in the myocardium. The likelihood of unintentionally perforating the myocardium to the epicardium is reduced when the depth of wound created is only enough to penetrate the endocardium.

Although breaking through the endocardium may be sufficient treatment for many patients, for some patients a physician may desire to penetrate the myocardium with electrode 30 a certain distance. As described previously, the depth which electrode 30 penetrates the heart tissue, may be controlled by the geometry of electrode 30 and landing zones 60. A number of models of catheter 20 may be provided to a physician, each model being adapted to create wounds of a particular depth. The depth of wound created is influenced by the depth which electrode 30 penetrates heart tissue. Other factors may influence wound depth without deviating from the spirit and scope of the present invention. For example, the magnitude and frequency of the radiofrequency energy applied to electrode 30 may effect the depth of wound created during a PMR procedure. By way of a second example, the length of time electrode 30 is energized may effect the depth of wound created.

In a presently preferred method, a fluid under pressure is forced into the wound by way of shaft lumen 36 and insulator lumens 34. This fluid may include saline, radiopaque contrast media, a therapeutic agent, a caustic agent, or any combination of these.

The formation of the wound may be enhanced by collateral damage to the myocardium induced by directing this pressurized fluid into the wound site. The impact of the pressurized fluid causes vessels, capillaries, and sinuses to rupture. By creating this collateral damage, the number of wounds which must be made during a PMR procedure can be substantially reduced. Injecting a fluid including a radiopaque contrast media into the wound serves to create a radiopaque marker of the treatment site. Injecting a fluid, including a therapeutic agent, serves to promote angiogenisis.

Forcing fluid under pressure into the wound may be used to create collateral damage. Collateral damage is created when vessels, capillaries, and sinuses within the myocardium are ruptured. Thus collateral damage will increase the healing response of the body. The fluid under pressure may be forced into the wound while electrode 30 is energized or during a time when electrode 30 is not energized. In either case, the distal end of catheter 20 is positioned proximate the wound. Because electrode 30 was used to create the wound, catheter 20 is in an ideal position to inject fluid into the wound. If a separate catheter was used to deliver fluid, the distal end of that catheter would need to be positioned over the wound.

A PMR system for use with catheter 20 may include a means for controlling the flow of fluid through catheter 20. In one embodiment of the invention, the means for controlling would direct fluid to be injected into the wound immediately after each spark. In a second envisioned embodiment of the present invention, a PMR system for use with catheter 20 would include a foot pedal capable of activating the means for controlling fluid flow, and the means for energizing electrode 30. In this embodiment of the present invention, fluid would flow from the distal end of catheter 20 while electrode 30 was energized. Several other embodiments of the means for controlling fluid flow are possible without deviating from the spirit or scope of the present invention. For example, fluid may be delivered a set time after energy is delivered.

A second benefit of collateral damage is that it may reduce the wound depth needed to create clinically effective results. The depth of the wound may be limited so that the wound just passes through the endocardium. Once the endocardium is perforated, pressure from infused fluid may be used to rupture myocardial vessels, capillaries and sinuses without further ablation or removal of tissue. As discussed previously, limiting the depth of ablation reduces the likelihood of unintentional myocardial perforation.

Those with skill in the art will appreciate that catheter 20 may also be used in procedures where collateral damage is deemed undesirable. Collateral damage may be avoided by not delivering fluid through catheter 20, or by delivering fluid through catheter 20 at a relatively low pressure. In addition to promoting increased blood flow, it is also believed that PMR improves a patient's condition through denervation. Specifically, the PMR induced wounds result in elimination of nerve endings which were previously sending pain signals to the brain as a result of hibernating tissue.

As described previously, increased blood flow to the myocardium is caused in part by the healing response to wound formation during PMR. Specifically, the formation of new vessels or capillaries is believed to occur in response to a newly created wound. The revascularization of myocardial tissue may be promoted by delivering a therapeutic agent to the wound area. Examples, of therapeutic agents include growth factors, drugs and caustic agents. In one embodiment of the present invention, the PMR procedure includes the step of delivering a therapeutic agent to the wound site via catheter 20. Shaft lumen 36 and insulator lumens 34 of catheter 20 provide a suitable channel for delivering a therapeutic agent to the wound site from a location outside the patient's body.

Fluids delivered via catheter 20 during a PMR procedure may provide additional benefits. For example, fluid delivered via catheter 20 may serve to cool electrode 30 during a PMR procedure. As a second example, fluid delivered via catheter 20 may serve to remove debris from the wound. It should be understood that steps may be omitted from the method described above, or the order of the steps may be changed without deviating from the spirit or scope of the present invention.

Those with skill in the art will recognize that catheter 20 may be used with bipolar or mono-polar PMR techniques. In a mono-polar PMR procedure, a return or neutral electrode is generally attached to the exterior of the patient. In a bi-polar PMR technique, a return or neutral electrode is positioned in close proximity to distal end 18 of catheter 20. For example, a tubular return electrode may be disposed on the outer surface of catheter 20 proximate its distal end 18.

Figure 3:
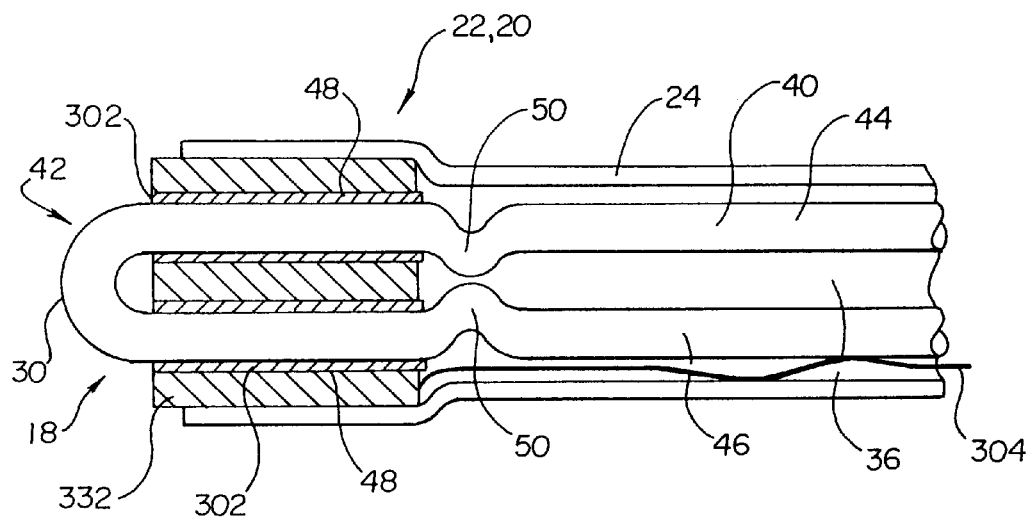
FIG. 3 is a plan view of a distal portion 22 of a catheter 20 in accordance with a bi-polar embodiment of the present invention.

A bi-polar embodiment of the present invention is illustrated if FIG. 3. FIG. 3 is a plan view of a distal portion 22 of a catheter 20. As in the embodiment of FIGS. 1 and 2, catheter 20 includes an elongate shaft 24, a proximal end 26 (not shown), and a distal portion 22. An electrode portion 30 and a return electrode 332 are disposed proximate a distal end 18 of catheter 20.

As shown in FIG. 3, elongate shaft 24 includes a lumen 36. Catheter 20 includes a conductor 40 having a bent portion 42, a first leg 44, and a second leg 46. First leg 44 and second leg 46 are disposed in lumen 36. Electrode 30 of catheter 20 is generally formed from bent portion 42 of conductor 40. Return electrode 332 defines two holes 48. Two sleeves 302 are disposed inside holes 48. First leg 44 and second leg 46 pass through sleeves 302. In the embodiment of FIG. 3, return electrode 332 is comprised of a conductive material allowing it to serve as a return electrode in a bi-polar PMR configuration. Sleeves 302 are comprised of a non-conductive material, and serve to insulate conductor 40 from return electrode 332. A return conductor 304 is coupled to return electrode 332. Return conductor 332 is suitably insulated so that it will not make electrical contact with conductor 40. In one envisioned embodiment of the present invention, return conductor 332 is disposed in a separate lumen of elongate shaft 24.

Figure 4:
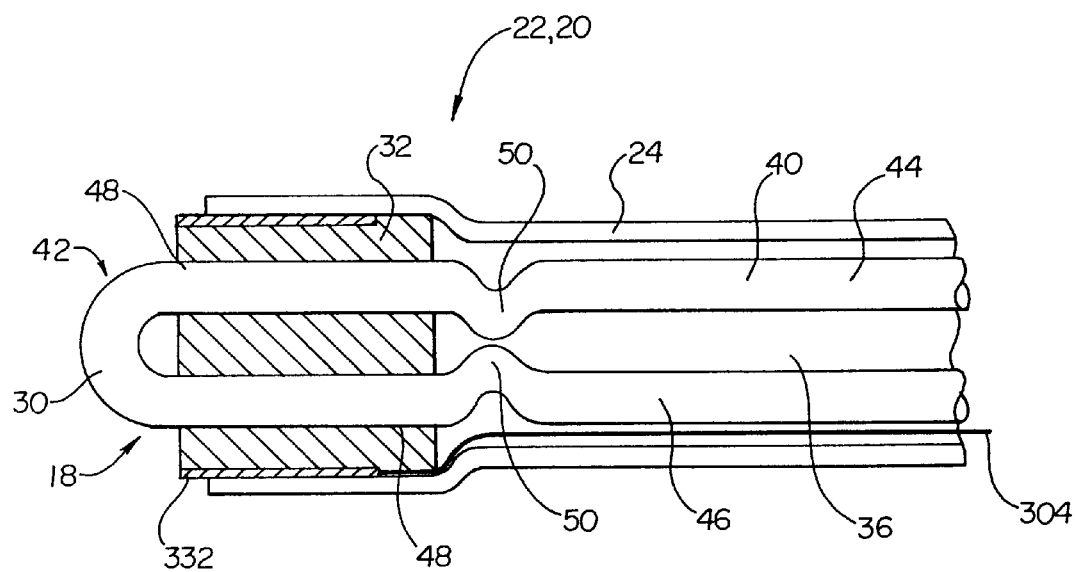
FIG. 4 is a plan view of a distal portion 22 of a catheter 20 in accordance with a further bi-polar embodiment of the present invention.

FIG. 4 is a plan view of a distal portion 22 of a catheter 20 in accordance with a bi-polar embodiment of the present invention. As in the embodiment of FIGS. 1 and 2, catheter 20 includes an elongate shaft 24, a proximal end 26 (not shown), and a distal portion 22. An electrode portion 30 and an insulator 32 are disposed proximate a distal end 18 of catheter 20.

As shown in FIG. 4, elongate shaft 24 includes a lumen 36. Catheter 20 includes a conductor 40 having a bent portion 42, a first leg 44, and a second leg 46. First leg 44 and second leg 46 are disposed in lumen 36. Electrode 30 of catheter 20 is generally formed from bent portion 42 of conductor 40. Insulator 32 defines two holes 48 which are adapted to allow legs 44, 46 of conductor 40 to pass through insulator 32.

In the embodiment of FIG. 4, a return electrode 332 is disposed about the outer surface of insulator 32. Return electrode 332 is comprised of a conductive material allowing it to serve as a return electrode in a bi-polar PMR configuration. A return conductor 304 is coupled to return electrode 332. Return conductor 332 is suitably insulated so that it will not make electrical contact with conductor 40. In one envisioned embodiment of the present invention, return conductor 332 is disposed in a separate lumen of elongate shaft 24. As shown in FIG. 4, return electrode 332 protrudes beyond the distal end of elongate shaft 24.

Figure 5:
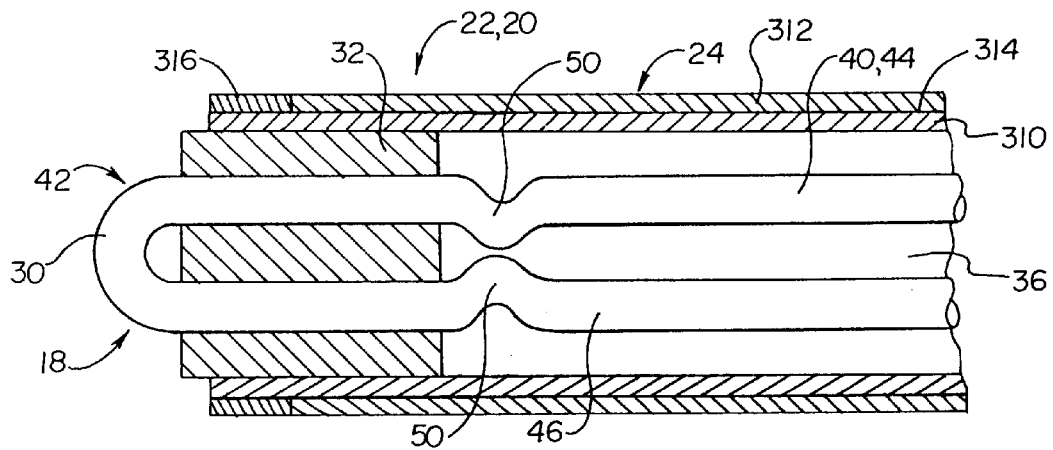
FIG. 5 is a plan view of a distal portion 22 of a catheter 20 in accordance with an additional bi-polar embodiment of the present invention.

FIG. 5 is a plan view of a distal portion 22 of a catheter 20 in accordance with a bi-polar embodiment of the present invention. As in the embodiment of FIGS. 1 and 2, catheter 20 includes an elongate shaft 24, a proximal end 26 (not shown), and a distal portion 22. An electrode portion 30 and an insulator 32 are disposed proximate a distal end 18 of catheter 20.

In the embodiment of FIG. 5, elongate shaft 24 is comprised of an outer tubular member 312 and an inner tubular member 310 having a lumen 36. A conductive coating 314 is disposed on the outer diameter of inner tubular member 310. Outer tubular member 312 is comprised of a nonconductive material and generally overlays conductive coating 314. In one embodiment outer tubular member 312 is comprised of shrink tubing. In a second embodiment outer tubular member 312 is comprised of a nonconductive coating. A portion of conductive coating 314 proximate distal end 18 is not covered by outer tubular member 312. Embodiments of the present invention have been envisioned in which exposed portions of conductive coating 314 act as a return electrode. In the embodiment of FIG. 5, a return electrode 316 is disposed about and electrically coupled to conductive coating 314. In a presently preferred embodiment, return electrode 316 is comprised of a material which is conductive and radiopaque. Examples of suitable materials include gold, platinum, silver, and tungsten.

In the embodiment of FIG. 5, conductive coating 314 acts as an electrical conductor coupling return electrode 316 to the radio frequency generator used in a PMR procedure. Catheter 20 of FIG. 5 also includes an electrode 30 generally formed from bent portion 42 of conductor 40. In one embodiment of the present invention, conductor 40 is electrically coupled to a radio frequency generator (not shown) by a cable (not shown). In a presently preferred embodiment, conductor 40 is directly attached to the cable.

Figure 6:
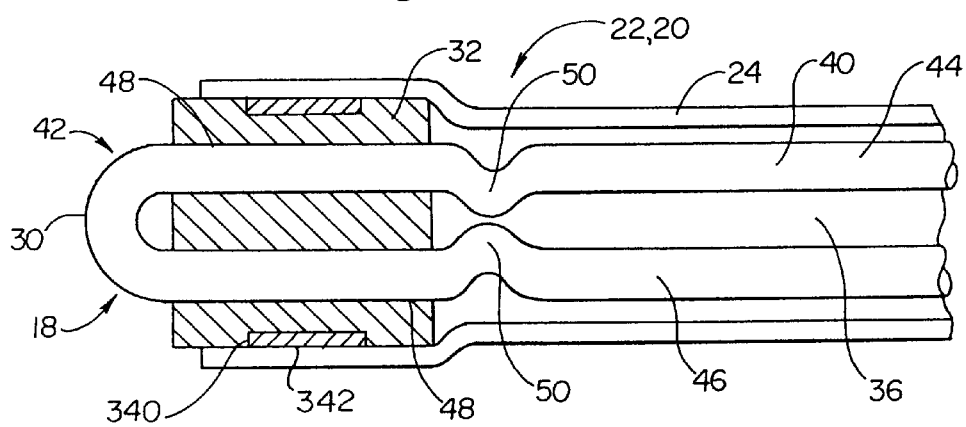
FIG. 6 is a plan view of the distal end of a catheter in accordance with the present invention.

FIG. 6 is a plan view of a distal portion 22 of a catheter 20 in accordance with one embodiment of the present invention. As in the embodiment of FIGS. 1 and 2, catheter 20 includes an elongate shaft 24, a proximal end 26 (not shown), and a distal portion 22. An electrode portion 30 and a insulator 32 are disposed proximate a distal end 18 of catheter 20.

As shown in FIG. 6, elongate shaft 24 includes a lumen 36. Catheter 20 includes a conductor 40 having a bent portion 42, a first leg 44, and a second leg 46. First leg 44 and second leg 46 are disposed in lumen 36. Electrode 30 of catheter 20 is generally formed from bent portion 42 of conductor 40. Insulator 32 defines two holes 48 which are adapted to allow legs 44, 46 of conductor 40 to pass through insulator 32. A groove 340 is disposed on the outer diameter of insulator 32. A band 342 is disposed in groove 340. In a presently preferred embodiment, band 342 is comprised of a radiopaque material. When radiographic equipment is used in conjunction with catheter 20, band 342 aids the physician in locating distal end 18 of catheter 20. Band 342 may be comprised of a number of radiopaque materials including gold, platinum, silver, tungsten, barium sulfate, and bismuth oxide. In a presently preferred embodiment, band 342 is a platinum/iridium blend.

Figure 7:
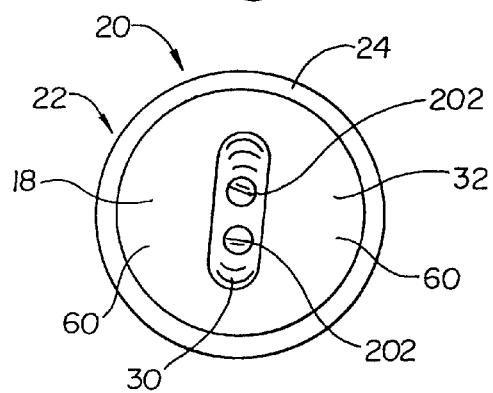
FIG. 7 is a plan view of the distal end of a catheter in accordance with the present invention.
Figure 8:
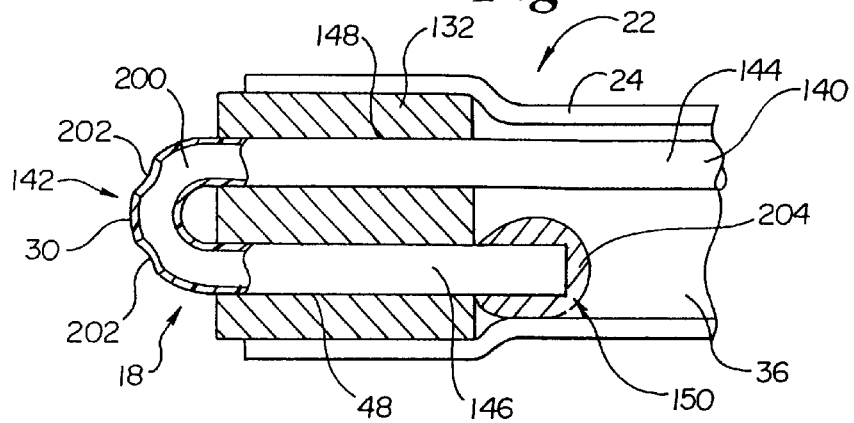
FIG. 8 is a plan view of a distal portion of a catheter in accordance with the present invention with the catheter being shown in partial cross section.

Referring now to FIGS. 7 and 8, which illustrate an additional embodiment of catheter 20. FIG. 8 is a plan view of distal portion 22 of catheter 20 shown in partial cross section. FIG. 7 is a plan view of distal end 18 of the embodiment of catheter 20 shown in FIG. 8. As in the previous embodiment, catheter 20 includes an elongate shaft 24, a proximal end 26 (not shown), a distal portion 22, and a distal end 18. An electrode portion 30 and an insulator 32 are disposed proximate distal end 18 of catheter 20. As best seen in FIG. 7, insulator 32 includes two landing zones 60 which extend away from electrode 30.

As best shown in FIG. 8, elongate catheter 20 includes a conductor 140 having a bent portion 142, a first leg 144, and a second leg 146. Conductor 140 also defines a lumen 200 and two holes 202 which are in fluid communication with lumen 200. Holes 202 in conductor 40 are shown most clearly in FIG. 7.

First leg 144 and second leg 146 are disposed in lumen 36 of elongate shaft 24. Electrode 30 is generally formed from bent portion 142 of conductor 140. As best shown in FIG. 8, insulator 32 defines two holes 48 which are adapted to allow legs 144, 146 of conductor 140 to pass through insulator 32.

A retaining element 150 is formed on conductor 140 proximate insulator 32. In the embodiment of FIG. 8, retaining element 150 has been created by forming a weld bead 204 on conductor 140. Weld bead 204 may be formed using a number of manufacturing processes. For example, welding, solder, and brazing are all suitable processes of creating weld bead 204. It will be understood that other embodiments of retaining element 150 are possible without deviating from the spirit or scope of the present invention. In the embodiment of FIGS. 3 and 4, weld bead 204 also serves the function of sealing the end of lumen 200.

As in the previous embodiment, electrode 30 protrudes beyond insulator 32 of catheter 20. The distance which electrode 30 protrudes is determined in part by the shape of bent region 142 of conductor 140. The distance which electrode 30 protrudes is carefully controlled during the manufacture of catheter 20. This helps to control the depth of the wounds created by catheter 20 during a PMR procedure. During such a procedure electrode 30 will proceed to penetrate the heart until insulator 32 contacts the heart tissue.

As best seen in FIG. 7, insulator 32 includes two landing zones 60 which extend away from electrode 30. The width of landing zones 60 is substantially greater than the width of electrode 30 in FIG. 7. The relatively large area of landing zones 60 assure that the travel of electrode 30 into the heart tissue will stop when landing zones 60 w contact the heart tissue. It is a desirable feature of this invention that landing zones 60 generally extend beyond the wound created in the heart tissue created during a PMR procedure. This is because the wounded tissue is substantially softened, and it is possible for a PMR catheter to be pushed through soft, injured tissue.

The distance which electrode 30 protrudes from landing zones 60 and the relative surface areas of these elements are carefully selected to create a therapeutically effective wound while reducing the likelihood of unintentionally perforating the myocardium. Preferably, a therapeutically effective wound will at a minimum perforate through the endocardium and damage blood vessels and capillaries in the myocardium. The likelihood of unintentionally perforating through the myocardium to the epicardium is reduced when the depth of wound created is only enough to penetrate the endocardium.

During a PMR procedure, catheter 20 is preferably advanced through the vasculature of a patient until distal end 18 is proximate the endocardium of the patient's heart. The route taken by catheter 20 will normally be by way of the femoral artery and the aorta to the left ventricle. Those with skill in the art will appreciate that other routes may be taken by catheter 20 without deviating from the spirit or scope of the present invention. For example, the right ventricle may be accessed via the pulmonary vein or the femoral vein. By way of a second example, the septal approach may be used. In a septal approach, the distal end of catheter 20 first enters one ventricle (the left or the right). A PMR procedure may be performed in that ventricle. The distal end of catheter 20 may then enter the other ventricle by passing through the septal wall. A third example of a route which may be taken by catheter 20 is a route via the carotid artery.

To facilitate the advancement of catheter 20 through the vasculature of the patient, catheter 20 may include a slippery material disposed on the outer surfaces of elongate shaft 24. Once inside the heart, distal end 18 of catheter 20 is positioned proximate the endocardium, preferably, such that electrode portion 30 is in contact with the endocardium. Contact between the endocardium and electrode 30 may be detected electronically. A method is further detailed in co-pending U.S. patent application Ser. No. 09/256,958, filed by the same assignee on even date herewith and entitled "Device and Method for Percutaneous Myocardial Revascularization.". The disclosure of this co-pending application is hereby incorporated by reference into the present application.

An additional method which may be used to determine the location of electrode 30 is through radiographic techniques. The use of radiographic techniques may be enhanced by selectively incorporating radiopaque material into catheter 20. In one embodiment of the present invention, a radiopaque material is disposed about the outer diameter of insulator 32. The radiopaque material may be comprised of a band of metal. Materials which may be suitable for this marker band include: gold, platinum, silver, and tungsten. A radiopaque material may also be included in electrode 30 and/or insulator 32.

Typically, an additional step in a method in accordance with the present invention is to identify areas of tissue within the patient's heart which are candidates for PMR. To facilitate ease of discussion, areas of tissue in the heart muscle may be generally classified healthy or hibernating. Healthy tissue is tissue which is well perfused with blood, and subsequently well supplied with oxygen. Hibernating tissue is tissue which is not currently contracting to assist in the pumping of blood. However, if hibernating tissue is adequately supplied with blood, it will once again begin contracting and contribute to the pumping of blood.

A number of methods may be used to identify hibernating tissue. For example, contrast media may be injected into the coronary vessels to identify regions of the heart into which the contrast medium does not flow due to obstruction of the vessels into which the media was injected. In this case, the hibernating region will be identified by the lack of flow or abnormally low flow distally of the obstruction in the coronary vessel or vessels.

A second method which may be used to identify hibernating regions of the heart involves injecting contrast media directly into the heart chambers. Hibernating tissue may then be identified by locating areas of generally poor wall motion of the heart chambers. When this method is selected, the contrast media may be delivered to the heart chambers via catheter 20. Lumen 200 and holes 202 of conductor 140 provide a channel for delivering contrast media from a location outside the patients body to distal end 18 of catheter 20.

Once hibernating regions within the heart area identified, these regions are candidates for PMR. During the PMR procedure, electrode 30 will proceed to penetrate the heart until landing zones 60 of insulator 32 contact the heart tissue. As described above, landing zones 60 have a relatively large surface area to assure that the depth of the wound will be controlled. The depth of the wound is also controlled by the distance which electrode 30 protrudes from landing zones 60. As described above, this distance is carefully controlled during the manufacture of catheter 20.

As described above, the distance which electrode 30 protrudes from landing zones 60 and the relative surface areas of these elements are carefully selected to create a therapeutically effective wound while reducing the likelihood of unintentionally perforating the myocardium. Preferably, a therapeutically effective wound generally will, at a minimum, perforate through the endocardium and damage blood vessels and capillaries in the myocardium. The likelihood of unintentionally perforating through the myocardium to the epicardium is reduced when the depth of wound created is only enough to penetrate the endocardium.

In a presently preferred method, a fluid under pressure is forced into the wound through lumen 200 and holes 202 of conductor 140. This fluid may include saline, contrast media, a therapeutic agent, a caustic agent, or any combination of these. By forcing fluid under pressure into the wound, vessels, capillaries, and sinuses in the myocardium will be collaterally damaged within an area proximate the wound. This collateral damage will increase the healing response by angiogenesis. The fluid under pressure may be forced into the wound while electrode 30 is energized, or during a time when electrode 30 is not energized.

The formation of the wound may be enhanced by collateral damage to the myocardium induced by directing this pressurized fluid into the wound site. The impact of the pressurized fluid causes vessels, capillaries, and sinuses to rupture. By creating this collateral damage, the number of wounds which need to be made during a PMR procedure may be substantially reduced.

A second benefit of collateral damage is that it may reduce the wound depth needed to create clinically effective results. The depth of the wound may be limited so that the wound just passes through the endocardium. Once the endocardium is perforated, pressure from infused fluid may be used to rupture the myocardial vessels, capillaries and sinuses without further ablation or removal of tissue. Limiting the depth of ablation reduces the likelihood of unintentional myocardial perforation. In addition, the injection of a fluid containing a radiopaque contrast solution creates a fluoroscopic marker of the treatment location.

An additional benefit of having holes 202 disposed at the distal end of catheter 20 is that they permit the fluid to be injected into the wound immediately after it is created. This eliminates the need to withdraw catheter 20 and position a second catheter to deliver fluid to the wound.

As described previously, increased blood flow to the myocardium is caused in part by the healing response to wound formation during PMR. Specifically, the formation of new vessels or capillaries is believed to occur in response to a newly created wound. The revascularization of myocardial tissue may be promoted by delivering a therapeutic agent to the wound area. Examples, of therapeutic agents include growth factors and drugs. In one embodiment of the present invention, the PMR procedure includes the step of delivering a therapeutic agent though lumen 200 and holes 202 of conductor 140.

In a presently preferred method, a fluid is delivered via catheter 20 to the patient proximate the wound. This fluid may include saline, radiopaque contrast media, a therapeutic agent, a caustic agent, or any combination of these. Injecting a fluid including a radiopaque contrast media acts to create a radiopaque marker of the treatment site. Injecting a fluid into a wound which includes a therapeutic agent acts to enhance the angiogenisis response of the body. An embodiment of the present invention has been envisioned where the same control means which enables radiofrequency energy to energize electrode 30 may be used to enable fluid to be injected into the wound from the distal end of catheter 20. In a presently preferred embodiment, the control means of the PMR system directs fluid to be injected into the wound immediately after each spark. Fluids delivered via catheter 20 during a PMR procedure may provide additional benefits. For example, fluid delivered via lumen 200 of conductor 140 may serve to cool electrode 30 during a PMR procedure. As a second example, fluid delivered via catheter 20 may serve to remove debris from the wound. It should be understood that steps may be omitted from the method described above, or the order of the steps may be changed without deviating from the spirit or scope of the present invention.

Figure 9:
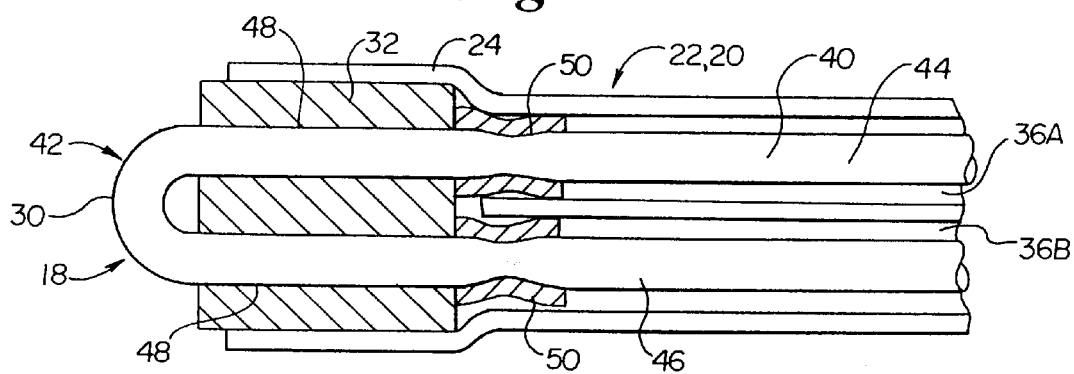
FIG. 9 is a plan view of the distal portion of a catheter in accordance with the present invention with the catheter being shown in partial cross section.

FIG. 9 is a plan view of a distal portion 22 of a catheter 20 in accordance with an alternate embodiment of the present invention. As in the previous embodiments catheter 20 includes an elongate shaft 24, a proximal end 26 (not shown), and a distal portion 22. An electrode portion 30 and an insulator 32 are disposed proximate a distal end 18 of catheter 20.

As shown in FIG. 9, elongate shaft 24 includes two lumens 36A, 36B. Catheter 20 includes a conductor 40 having a bent portion 42, a first leg 44, and a second leg 46. First leg 44 and second leg 46 are disposed in lumens 36A and 36B respectively. Electrode 30 of catheter 20 is general formed from bent portion 42 of conductor 40. Insulator 32 defines two holes 48 which are adapted to allow legs 44, 46 of conductor 40 to pass through insulator 32. Insulator 32 defines additional holes (not shown) which allow fluid to pass therethrough.

Two retaining elements 50 are located on conductor 40 proximate insulator 32. In the embodiment of FIG. 9, each retaining element 50 is a sleeve surrounding conductor 40. Each retaining element 50 has been fixed to conductor 40 with a crimping process. Retaining elements 50 assist in maintaining the position of bent portion 42; preventing it from moving before, or during a PMR procedure. Insulator 32, acting in conjunction with retaining elements 50, supports bent portion 42 of conductor 40, preventing it from being deformed during a PMR procedure.

Figure 10:
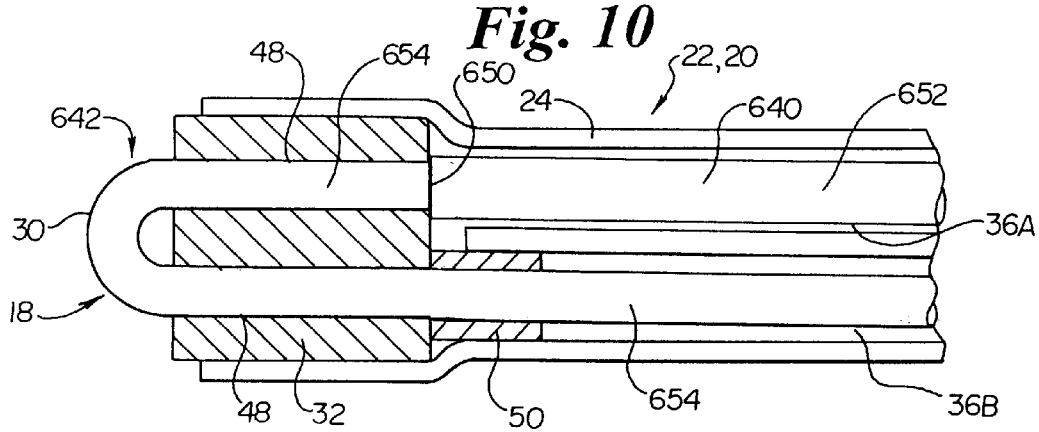
FIG. 10 is a plan view of the distal portion of a catheter in accordance with the present invention with the catheter shown in partial cross section.

FIG. 10 is a plan view of a distal portion 22 of a catheter 20 in accordance with an alternate embodiment of the present invention. As in the previous embodiments catheter 20 includes an elongate shaft 24, a proximal end 26 (not shown), and a distal portion 22. An electrode portion 30 and an insulator 32 are disposed proximate a distal end 18 of catheter 20.

Elongate shaft 24 includes two lumens 36A, 36B. Catheter 20 includes a conductor 640 having a bent portion 642, a first portion 652, and a second portion 654. As shown in FIG. 10, the outer diameter of second portion 654 is smaller than the outer diameter of first portion 652. Conductor 640 includes a step 650 proximate the intersection between first portion 652 and second portion 654.

First portion 652 of conductor 640 is substantially disposed in lumen 36A of elongate shaft 24. Second portion 654 of conductor 640 passes through insulator 32 via two holes 48. The remaining portion of second portion 654 is disposed in lumen 36B of elongate shaft 24. A bent portion 642 of conductor 640 extends beyond insulator 32; an electrode 30 is general formed by bent portion 642.

A retaining element 50 is located on second portion 654 proximate insulator 32. In the embodiment of FIG. 10, retaining element 50 is a sleeve surrounding conductor 640. A number of processes may be used to fix retaining element 50 onto conductor 640. For example, there may be an interference fit between the sleeve and conductor 640. Other examples of acceptable retention methods include soldering, brazing, welding, crimping, and adhering with an adhesive. Retaining element 50 and step 650 assist in maintaining the position of bent portion 642; preventing it from moving before, or during a PMR procedure. Insulator 32, acting in conjunction with retaining element 50, supports bent portion 642 of conductor 640, preventing it from being deformed during a PMR procedure.

FIG. 11 is a plan view of a distal portion 22 of a catheter 20 in accordance with an alternate embodiment of the present invention. As in the previous embodiments catheter 20 includes an elongate shaft 24, a proximal end 26 (not shown), and a distal portion 22. An electrode portion 30 and an insulator 32 are disposed proximate a distal end 18 of catheter 20.

As shown in FIG. 11, elongate shaft 24 includes a lumen 36. Catheter 20 includes a conductor 740 having a bent portion 742, a first leg 744, and a second leg 746. First leg 744 and second leg 746 are substantially disposed in lumen 36. Electrode 30 of catheter 20 is general formed by bent portion 742 of conductor 740. Insulator 32 defines two holes 48 which are adapted to allow legs 744, 746 of conductor 740 to pass through insulator 32.

A bond 750 is formed between first leg 744 and second leg 746 of conductor 740. A number of process may be used to create bond 750. For example, bond 750 may be created by applying an adhesive between first leg 744 and second leg 746. Other techniques which may be used to fabricate bond 750 include welding, brazing, and soldering.

FIG. 12 is a plan view of a distal portion 22 of a catheter 20 in accordance with an alternate embodiment of the present invention. As in the previous embodiments catheter 20 includes an elongate shaft 24, a proximal end 26 (not shown), and a distal portion 22. An electrode portion 30 and an insulator 32 are disposed proximate a distal end 18 of catheter 20.

As shown in FIG. 12, elongate shaft 24 includes two lumens 36A, 36B. Catheter 20 includes a conductor 40 having a bent portion 42, a first leg 44, and a second leg 46. First leg 44 and second leg 46 are substantially disposed in lumens 36A and 36B respectively. Electrode 30 of catheter 20 is general formed from bent portion 42 of conductor 40. Insulator 32 defines two holes 48 which are adapted to allow legs 44, 46 of conductor 40 to pass through insulator 32. 5 Two retaining elements 50 are located on conductor 40 proximate insulator 32. In the embodiment of FIG. 12, each retaining element 50 is formed from material of conductor 40 which has been displaced to create a localized area with a greater width. A crimping or staking process may be used to create deformations of this type in conductor 40.

Retaining elements 50 assist in maintaining the position of bent portion 42; preventing it from moving before, or during a PMR procedure. Insulator 32 acting in conjunction with retaining elements 50 supports bent portion 42 of conductor 40, preventing it from being deformed during a PMR procedure.

FIG. 13 is a plan view of a distal portion 22 of a catheter 20 in accordance with an alternate embodiment of the present invention. As in the previous embodiments catheter 20 includes an elongate shaft 24, a proximal end 26 (not shown), and a distal portion 22. An electrode portion 30 and an insulator 32 are disposed proximate a distal end 18 of catheter 20.

As shown in FIG. 13, elongate shaft 24 includes two lumens 36A, 36B. Catheter 20 includes a conductor 40 having a bent portion 42, a first leg 44, and a second leg 46. First leg 44 and second leg 46 are substantially disposed in lumens 36A and 36B respectively. Electrode 30 of catheter 20 is general formed from bent portion 42 of conductor 40.

Insulator 32 defines two holes 48 which are adapted to allow legs 44, 46 of conductor 40 to pass through insulator 32.

Conductor 40 is fixed to insulator 32 by two adhesive bonds 902A, 902B which prevent bent portion 42 from moving before, or during a PMR procedure. Insulator 32 acting in conjunction with adhesive bonds 902A, 902B supports bent portion 42 of conductor 40, preventing it from being deformed during a PMR procedure.

Figure 14:
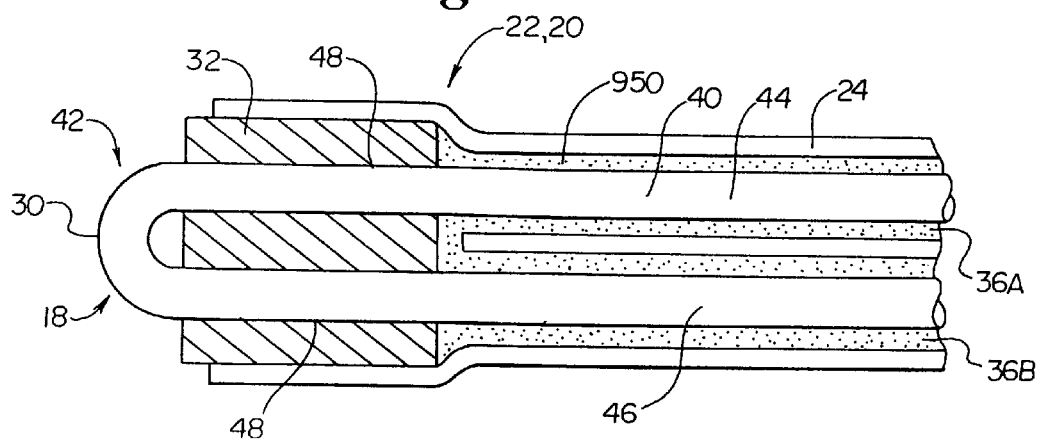
FIG. 14 is a plan view of the distal portion of a catheter in accordance with the present invention.

FIG. 14 is a plan view of a distal portion 22 of a catheter 20 in accordance with an alternate embodiment of the present invention. As in the previous embodiments catheter 20 includes an elongate shaft 24, a proximal end 26 (not shown), and a distal portion 22. An electrode portion 30 and an insulator 32 are disposed proximate a distal end 18 of catheter 20.

As shown in FIG. 14, elongate shaft 24 includes two lumens 36A, 36B. Catheter 20 includes a conductor 40 having a bent portion 42, a first leg 44, and a second leg 46. First leg 44 and second leg 46 are substantially disposed in lumens 36A and 36B respectively. Electrode 30 of catheter 20 is general formed from bent portion 42 of conductor 40. Insulator 32 defines two holes 48 which are adapted to allow legs 44, 46 of conductor 40 to pass through insulator 32.

In the embodiment of FIG. 14, lumens 36A, 36B of elongate shaft 24 are substantially filled with potting material 950. Potting material 950 serves to fix the location of conductor 30 relative to insulator 32 and elongate shaft 24. Potting material 950 may be comprised of a number of materials. Examples of suitable materials include silicone rubber and urethane. Catheter 20 and insulator 32 may include additional lumens (not shown in FIG. 14) which allow a fluid to be conducted from proximal end 26 of catheter 20 to distal end 18 of catheter 20.

Figure 15:
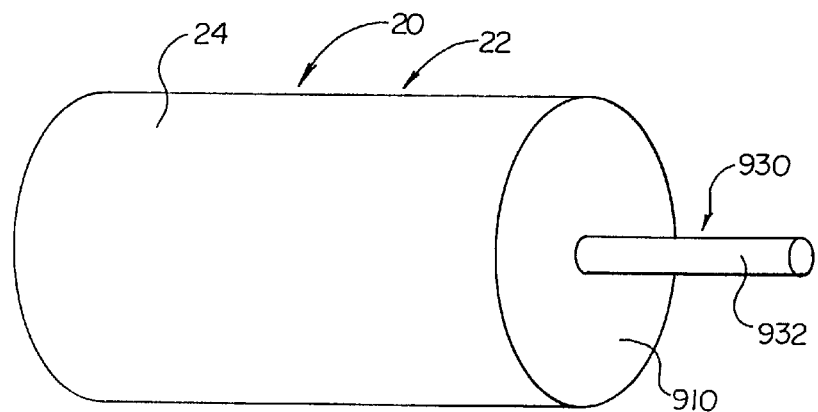
FIG. 15 is a perspective view of the distal end of the catheter including an alternate electrode assembly.

FIG. 15 is a perspective view of a distal portion 22 of a catheter 20 in accordance with an alternate embodiment of the present invention. As in the previous embodiments catheter 20 includes an elongate shaft 24, a proximal end 26 (not shown), and a distal portion 22. Elongate shaft 24 includes a distal end 910. An electrode 930 projects from distal end 910 of elongate shaft 24. In the embodiment of FIG. 15, electrode 930 is comprised of a conductor 932 which is generally cylindrical in shape. During a PMR procedure in accordance with a presently preferred embodiment of the present invention, electrode 930 is energized with radio frequency energy causing it to create a wound. During wound formation, electrode 930 penetrates the tissue of the heart. Electrode 930 continues penetrating heart tissue until distal end 910 of elongate shaft 24 contacts the surface of the heart tissue.

Figure 16:
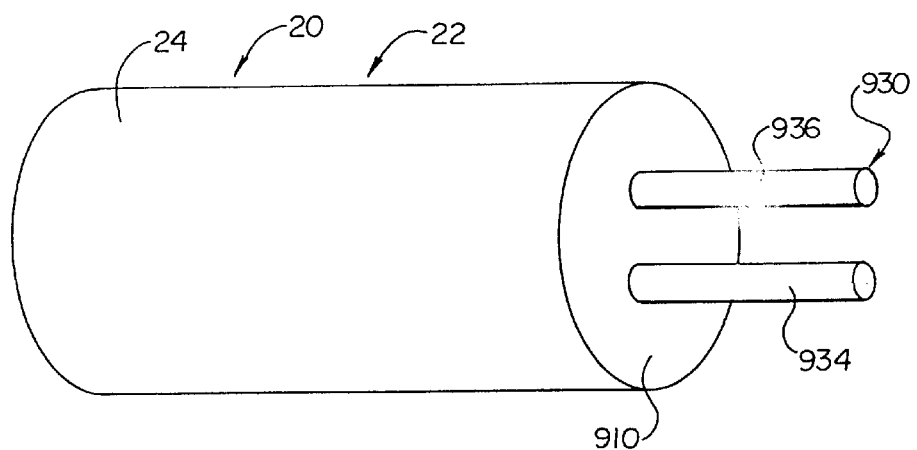
FIG. 16 is a perspective view of the distal end of a catheter including a further alternate embodiment of an electrode assembly.

FIG. 16 is a perspective view of a distal portion 22 of a catheter 20 in accordance with an additional alternate embodiment of the present invention. As in the previous embodiments catheter 20 includes an elongate shaft 24, a proximal end 26 (not shown), and a distal portion 22. Elongate shaft 24 includes a distal end 910. An electrode 930 projects from distal end 910 of elongate shaft 24. In the embodiment of FIG. 16, electrode 930 is comprised of two conductors 934 and 936. Conductors 934 and 936 are both generally cylindrical in shape. During a PMR procedure in accordance with a presently preferred embodiment of the present invention, electrode 930 is energized with radio frequency energy causing it to create a wound. During wound formation, electrode 930 penetrates the tissue of the heart. Electrode 930 continues penetrating heart tissue until distal end 910 of elongate shaft 24 contacts the surface of the heart tissue.

Figure 17:
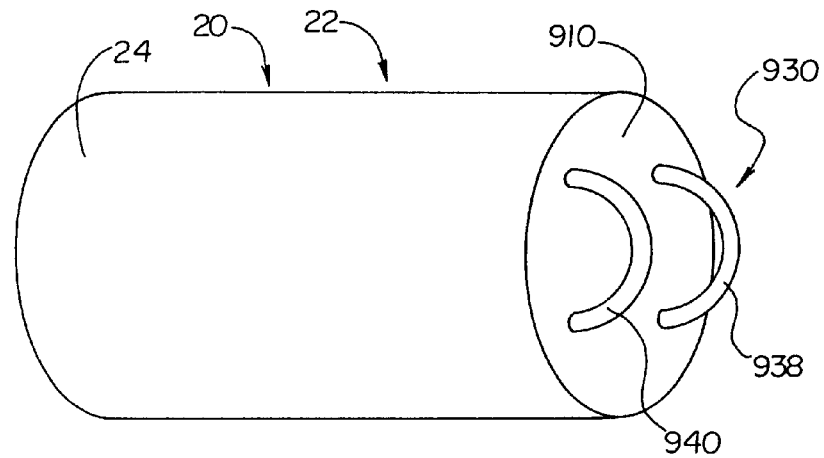
FIG. 17 is a perspective view of the distal end of a catheter including another embodiment of an electrode assembly.

FIG. 17 is a perspective view of a distal portion 22 of a catheter 20 in accordance with an additional alternate embodiment of the present invention. As in the previous embodiments catheter 20 includes an elongate shaft 24, a proximal end 26 (not shown), and a distal portion 22. Elongate shaft 24 includes a distal end 910. An electrode 930 projects from distal end 910 of elongate shaft 24. In the embodiment of FIG. 17, electrode 930 is comprised of two conductors 938 and 940. Conductors 938 and 940 are both generally arch shaped. During a PMR procedure in accordance with a presently preferred embodiment of the present invention, electrode 930 is energized with radio frequency energy causing it to create a wound. During wound formation, electrode 930 penetrates the tissue of the heart. Electrode 930 continues penetrating heart tissue until distal end 910 of elongate shaft 24 contacts the surface of the heart tissue.

Figure 18:
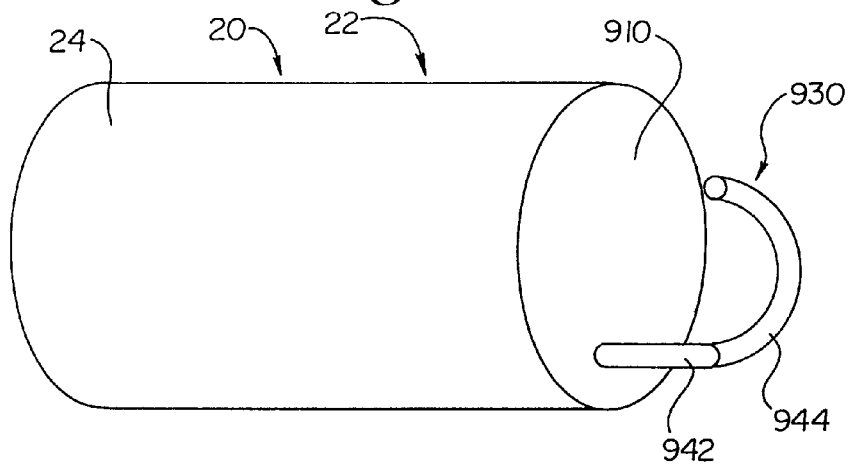
FIG. 18 is a perspective view of the distal end of the catheter including a further alternate embodiment of an electrode assembly.

FIG. 18 is a perspective view of a distal portion 22 of a catheter 20 in accordance with an additional alternate embodiment of the present invention. As in the previous embodiments catheter 20 includes an elongate shaft 24, a proximal end 26 (not shown), and a distal portion 22. Elongate shaft 24 includes a distal end 910. An electrode 930 projects from distal end 910 of elongate shaft 24. In the embodiment of FIG. 18, electrode 930 is comprised of a straight portion 942 and a curved portion 944. During a PMR procedure in accordance with a presently preferred embodiment of the present invention, electrode 930 is energized with radio frequency energy causing it to create a wound. During wound formation, electrode 930 penetrates the tissue of the heart. Electrode 930 continues penetrating heart tissue until distal end 910 of elongate shaft 24 contacts the surface of the heart tissue.

Figure 19:
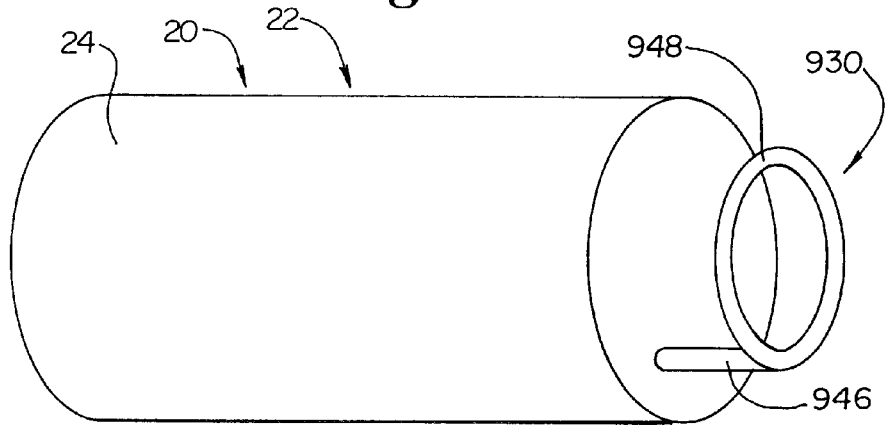
FIG. 19 is a perspective view of the distal end of a catheter including a further alternate embodiment of an electrode assembly.

FIG. 19 is a perspective view of a distal portion 22 of a catheter 20 in accordance with an additional alternate embodiment of the present invention. As in the previous embodiments catheter 20 includes an elongate shaft 24, a proximal end 26 (not shown), and a distal portion 22. Elongate shaft 24 includes a distal end 910. An electrode 930 projects from distal end 910 of elongate shaft 24. In the embodiment of FIG. 19, electrode 930 is comprised of a straight portion 946 and a ring portion 948. During a PMR procedure in accordance with a presently preferred embodiment of the present invention, electrode 930 is energized with radio frequency energy causing it to create a wound. During wound formation, electrode 930 penetrates the tissue of the heart. Electrode 930 continues penetrating heart tissue until distal end 910 of elongate shaft 24 contacts the surface of the heart tissue.

Figure 20:
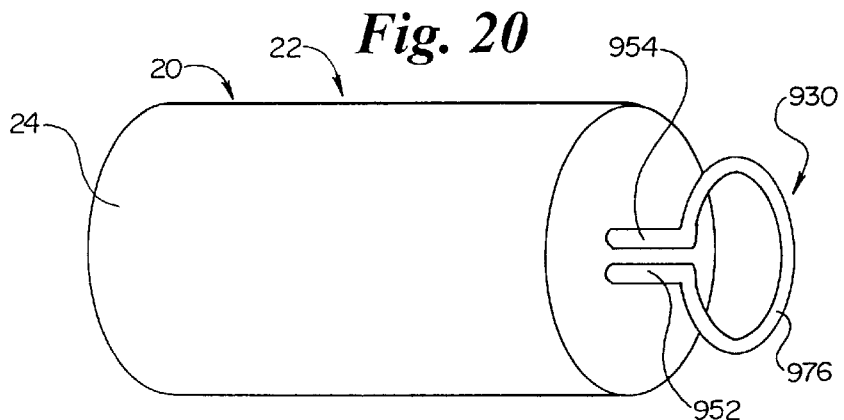
FIG. 20 is a perspective view of a distal end of a catheter including an alternate embodiment of an electrode assembly.

FIG. 20 is a perspective view of a distal portion 22 of a catheter 20 in accordance with an additional alternate embodiment of the present invention. As in the previous embodiments catheter 20 includes an elongate shaft 24, a proximal end 26 (not shown), and a distal portion 22. Elongate shaft 24 includes a distal end 910. An electrode 930 projects from distal end 910 of elongate shaft 24. In the embodiment of FIG. 20, electrode 930 includes two straight portions 952 and 954 projecting from distal end 910 of elongate shaft 24. Electrode 930 also includes a hoop portion 956 having two ends 958. One end 958 of hoop 956 is joined to the distal end of straight portion 952. The other end 958 of hoop 956 is joined to the distal end of straight portion 954. During a PMR procedure in accordance with a presently preferred embodiment of the present invention, electrode 930 is energized with radio frequency energy causing it to create a wound. During wound formation, electrode 930 penetrates the tissue of the heart. Electrode 930 continues penetrating heart tissue until distal end 910 of elongate shaft 24 contacts the surface of the heart tissue.

Figure 21:
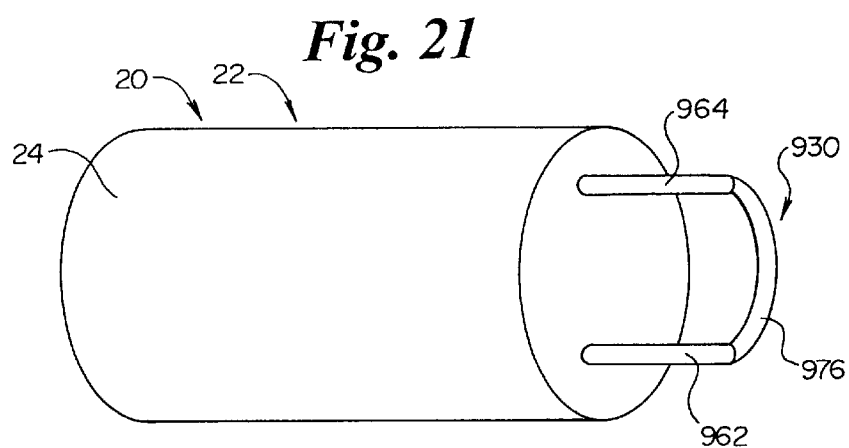
FIG. 21 is a perspective view of the distal end of a catheter including a further alternate embodiment of an electrode assembly.

FIG. 21 is a perspective view of a distal portion 22 of a catheter 20 in accordance with an additional alternate embodiment of the present invention. As in the previous embodiments catheter 20 includes an elongate shaft 24, a proximal end 26 (not shown), and a distal portion 22. Elongate shaft 24 includes a distal end 910. An electrode 930 projects from distal end 910 of elongate shaft 24. In the embodiment of FIG. 21, electrode 930 includes two straight portions 962 and 964 projecting from distal end 910 of elongate shaft 24. Electrode 930 also includes an interconnecting portion 966 having two ends 968. One end 968 of interconnecting portion 966 is joined to the distal end of straight portion 962. The other end 968 of interconnecting portion 966 is joined to the distal end of straight portion 964. In the embodiment of FIG. 21, interconnecting portion 966 is generally "U" shaped. During a PMR procedure in accordance with a presently preferred embodiment of the present invention, electrode 930 is energized with radio frequency energy causing it to create a wound. During wound formation, electrode 930 penetrates the tissue of the heart. Electrode 930 continues penetrating heart tissue until distal end 910 of elongate shaft 24 contacts the surface of the heart tissue.

Figure 22:
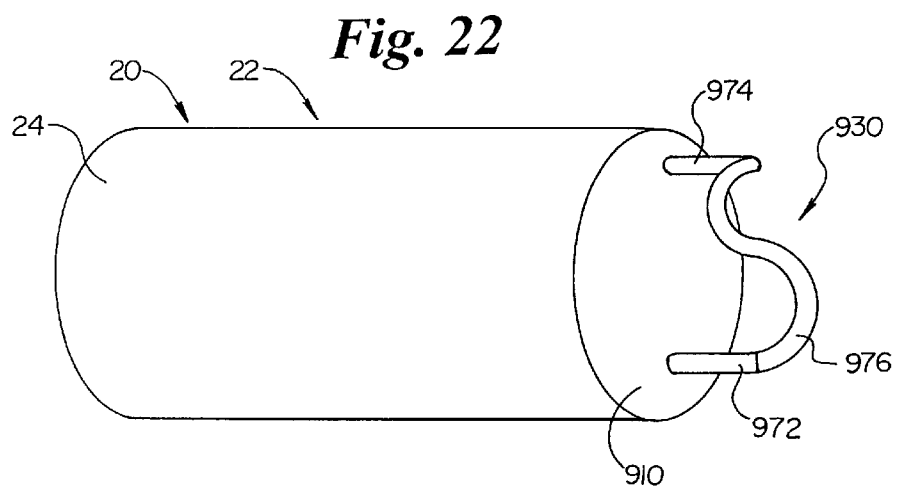
FIG. 22 is a perspective view of the distal end of a catheter including a further alternate embodiment of an electrode assembly.

FIG. 22 is a perspective view of a distal portion 22 of a catheter 20 in accordance with an additional alternate embodiment of the present invention. As in the previous embodiments catheter 20 includes an elongate shaft 24, a proximal end 26 (not shown), and a distal portion 22. Elongate shaft 24 includes a distal end 910. An electrode 930 projects from distal end 910 of elongate shaft 24. In the embodiment of FIG. 22, electrode 930 includes two straight portions 972 and 974 projecting from distal end 910 of elongate shaft 24. Electrode 930 also includes an interconnecting portion 976 having two ends 978. One end 978 of interconnecting portion 976 is joined to the distal end of straight portion 972. The other end 978 of interconnecting portion 976 is joined to the distal end of straight portion 974. In the embodiment of FIG. 22, interconnecting portion 976 is generally "S" shaped. During a PMR procedure in accordance with a presently preferred embodiment of the present invention, electrode 930 is energized with radio frequency energy causing it to create a wound. During wound formation, electrode 930 penetrates the tissue of the heart. Electrode 930 continues penetrating heart tissue until distal end 910 of elongate shaft 24 contacts the surface of the heart tissue.

Having thus described the preferred embodiments of the present invention, those of skill in the art will readily appreciate that yet other embodiments may be made and used within the scope of the claims hereto attached.

A PMR method in accordance with the present invention, may include the step of delivering a fluid to the wound site via catheter 102. This fluid may include saline, radiopaque contrast media, a therapeutic agent, a caustic agent, or any combination of these. Injecting a fluid including a radiopaque contrast media into the wound site serves to create a radiopaque marker of a treatment site. Injecting a fluid, including a therapeutic agent, serves to promote angiogenisis. The formation of the wound may also be enhanced by collateral damage to the myocardium induced by directing pressurized fluid into the wound site. The impact of the pressurized fluid causes vessels, capillaries, and sinuses to rupture.

Numerous advantages of the invention covered by this document have been set forth in the foregoing description.

It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A catheter assembly, comprising:
   an elongate shaft having a proximal end, and a distal end;
   a lumen defined by the elongate shaft and extending through at least a portion thereof;
   a conductor including a bent portion, a first leg portion, and a second leg portion;
   the bent portion of the conductor protruding from the distal end of the elongate shaft;
   a conductor lumen defined by the bent portion of the conductor, the conductor lumen being in fluid communication with the shaft lumen and
   an aperture defined by the bent portion of the conductor and in fluid communication with the conductor lumen.

2. The catheter assembly of claim 1, further including at least one retaining element disposed on the conductor proximate the distal end of the elongate shaft.

3. The catheter assembly of claim 2, wherein at least one retaining element is a crimp.

4. The catheter assembly of claim 2, wherein at least one retaining element is a weld bead.

5. The catheter assembly of claim 2, wherein at least one retaining element is a sleeve.

6. The catheter assembly of claim 2, wherein at least one retaining element is a kink.

7. The catheter assembly of claim 2, wherein at least one retaining element is a step.

8. The catheter assembly of claim 2, wherein at least one retaining element is a filler.

9. The catheter assembly of claim 2, wherein at least one retaining element is a localized area of greater width.

10. The catheter assembly of claim 1, wherein the conductor includes at least one tapered section.

11. The catheter assembly of claim 1, wherein the conductor is comprised of stainless steel.

12. The catheter assembly of claim 1, wherein the conductor is comprised of Nitinol.

13. The catheter assembly of claim 1, wherein the bent portion of the conductor is generally U shaped.

14. The catheter assembly of claim 1, further comprising a radio frequency generator connected to the conductor.

15. A catheter assembly, comprising:
   an elongate shaft having a proximal end, and a distal end;
   a lumen defined by the elongate shaft and extending through at least a portion thereof;
   an insulator fixedly attached to the elongate shaft proximate it's distal end;
   the insulator defining at least one hole;
   a conductor including a bent portion and at least one leg portion;
   the leg portion of the conductor passing through the hole of the insulator and being disposed in the shaft lumen;
   the bent portion of the conductor protruding from the distal end of the elongate shaft; and
   at least one retaining element disposed on the conductor proximate, and in interference with the insulator.

16. The catheter assembly of claim 15 further including a conductor lumen defined by the bent portion of the conductor;

an aperture defined by the bent portion of the conductor and in fluid communication with the conductor lumen; and the aperture and the conductor lumen being in fluid communication with the shaft lumen.

17. The catheter assembly of claim 15, wherein at least one retaining element is a crimp.

18. The catheter assembly of claim 15, wherein at least one retaining element is a weld bead.

19. The catheter assembly of claim 15, wherein at least one retaining element is a kink.

20. The catheter assembly of claim 15, wherein at least one retaining element is a step.

21. The catheter assembly of claim 15, wherein at least one retaining element is a localized area of greater width.

22. The catheter assembly of claim 15, wherein the conductor includes at least one tapered portion.

23. The catheter assembly of claim 15, wherein the conductor is comprised of stainless steel.

24. The catheter assembly of claim 15, wherein the conductor is comprised of Nitinol.

25. The catheter assembly of claim 15, further comprising a radio frequency generator connected to the conductor.

26. The catheter assembly of claim 15, wherein the bent portion of the conductor is generally U shaped.

27. A method of performing PMR, comprising the steps of:

providing a catheter including an elongate shaft having a proximal end, a distal end;

a conductor including a bent portion, a first leg portion, and a second leg portion;

the bent portion of the conductor defining a conductor lumen and a plurality of apertures in fluid communication with the conductor lumen;

the bent portion of the conductor protruding from the distal end of the elongate shaft;

positioning the distal end of the catheter proximate the endocardium of a patient's heart;

urging a fluid through the conductor lumen so that it exits the plurality of apertures; and energizing the conductor with radio frequency energy to perform PMR.

28. The method of claim 27, further comprising the step of providing landing zones proximate the distal end of the elongate shaft.

29. The method of claim 28, further comprising the step of adapting the landing zones to halt the travel of the conductor into heart tissue.

30. The method of claim 27, wherein the fluid includes a therapeutic agent.

31. The method of claim 30, wherein the therapeutic agent is a growth factor.

32. The method of claim 27, wherein the fluid includes a contrast media.

33. The method of claim 27, wherein the fluid includes saline.

* * * * *